United States Patent [19]

Cutler et al.

[11] B 3,988,370

[45] Oct. 26, 1976

[54] AMIDINOUREAS

[75] Inventors: Royal A. Cutler, Sand Lake; Samuel Schalit, Albany, both of N.Y.

[73] Assignee: Sterling Drug Inc., New York, N.Y.

[22] Filed: Aug. 24, 1973

[21] Appl. No.: 391,473

[44] Published under the second Trial Voluntary Protest Program on March 2, 1976 as document No. B 391,473.

Related U.S. Application Data

[60] Division of Ser. No. 79,266, Oct. 8, 1970, Pat. No. 3,798,269, which is a division of Ser. No. 749,986, Aug. 5, 1968, Pat. No. 3,652,766, which is a continuation-in-part of Ser. No. 556,897, June 13, 1966, abandoned, which is a continuation-in-part of Ser. No. 462,077, June 7, 1965, abandoned.

[52] U.S. Cl. .............................................. 260/553 R
[51] Int. Cl.$^2$ ...................................... C07C 127/15
[58] Field of Search ................................ 260/553 R

[56] References Cited

UNITED STATES PATENTS 3,798,269    3/1974    Cutler et al. ................... 260/553 R

FOREIGN PATENTS OR APPLICATIONS 954,114    4/1964    United Kingdom

OTHER PUBLICATIONS

Dutta et al., Journ. Indian Chem. Soc., vol. 36, No. 7, pp. 499–504, (1959).
Ray, Chemical Reviews, vol. 61, p. 323, (1961).

*Primary Examiner*—James O. Thomas, Jr.
*Assistant Examiner*—G. Breitenstein
*Attorney, Agent, or Firm*—B. Woodrow Wyatt; Theodore C. Miller

[57] ABSTRACT

Antibacterial and antifungal mono- and disubstituted amidinoureas and amidinothioureas are obtained by interaction of guanidines and isocyanates or isothiocyanates.

3 Claims, No Drawings

AMIDINOUREAS

This application is a division of copending application Ser. No. 79,266, filed Oct. 8, 1970 and now U.S. Pat. No. 3,798,269, which is a division of copending application Ser. No. 749,986, filed Aug. 5, 1968 and now U.S. Pat. No. 3,652,766, which is a continuation-in-part of copending application Ser. No. 556,897, filed June 13, 1966 and now abandoned, which is a continuation-in-part of copending application Ser. No. 462,077, filed June 7, 1965 and now abandoned.

This invention relates to chemical compounds classified as amidinoureas and amidinothioureas, to the preparation of the same and to a process for combatting microorganisms therewith.

The invention sought to be patented, in its process aspect, is described as residing in the concept of applying to a medium, in order to obviate objectionable or deleterious microorganisms, a composition of matter containing a chemical compound selected either from the group of compounds which, in the form of the free base, has the structural formula

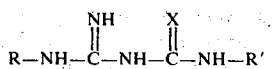

FORMULA I wherein X is a member of the group consisting of oxygen and sulfur and one of R and R' is alkyl and the other of R and R' is a member of the group consisting of hydrogen and alkyl, the total number of carbon atoms in R and R' being 8–24; or from the group of compounds which, in the form of the free-base, has the structural formula

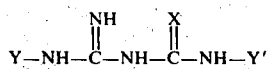

FORMULA II wherein: X is a member of the group consisting of oxygen and sulfur; one of Y and Y' is a member of the group consisting of hydrogen, alkyl containing 1–18 carbon atoms, alkenyl containing 3–18 carbon atoms, alkoxyalkyl containing 3–17 carbon atoms, alkylthioalkyl containing 3–17 carbon atoms, cycloalkyl containing 3–8 carbon atoms, di(lower alkyl)aminoalkyl containing 4–10 carbon atoms, morpholinoalkyl containing 6–10 carbon atoms, and piperidinoalkyl containing 7–11 carbon atoms; and the other of Y and Y' is a member of the group consisting of alkenyl containing 3–18 carbon atoms, alkoxyalkyl containing 3–17 carbon atoms, alkylthioalkyl containing 3–17 carbon atoms, cycloalkyl containing 3–8 carbon atoms, di(lower alkyl)aminoalkyl containing 4–10 carbon atoms, morpholinoalkyl containing 6–10 carbon atoms, and piperidinoalkyl containing 7–11 carbon atoms.

The invention sought to be patented, in its composition aspect, is described as residing in the concept of a chemical compound having the structural formula

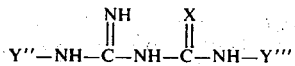

FORMULA III wherein: X is oxygen or sulfur; Y'' and Y'''may be the same or different and are members of the group consisting of alkyl containing 1–18 carbon atoms, alkenyl containing 3–18 carbon atoms, alkoxyalkyl containing 3–17 carbon atoms, alkylthioalkyl containing 3–17 carbon atoms, cycloalkyl containing 3–8 carbon atoms, di(lower alkyl)aminoalkyl containing 4–10 carbon atoms, morpholinoalkyl containing 6–10 carbon atoms or piperidinoalkyl containing 7–11 carbon atoms; Y'' also is hydrogen when X is oxygen and Y''' is alkenyl containing 3–18 carbon atoms, alkylthioalkyl containing 3–17 carbon atoms, di(lower alkyl)aminoalkyl containing 4–10 carbon atoms, morpholinoalkyl containing 6–10 carbon atoms or piperidinoalkyl containing 7–11 carbon atoms; and Y'' also is hydrogen when X is sulfur and Y''' is alkyl containing 8–18 carbon atoms, alkoxyalkyl containing 3–17 carbon atoms, alkylthioalkyl containing 3–17 carbon atoms, cycloalkyl containing 3–8 carbon atoms, di(lower alkyl)aminoalkyl containing 4–10 carbon atoms, morpholinoalkyl containing 6–10 carbon atoms or piperidinoalkyl containing 7–11 carbon atoms.

The compounds of Formulas I, II and III are basic substances which interact with one or, in the instances of the morpholinoalkyl and piperidinoalkyl compounds, two or three equivalents of an organic or inorganic acid to form the corresponding acid-addition salts. These acid-addition salts and the free bases of course have the common structural entity represented by the structural formulas, Formula I, Formula II, or Formula III, as the case may be. The acid-addition salts are the full equivalents of the free base forms, and the new compounds of this invention include both the free bases and the acid-addition salts thereof. The novel feature of the compounds of the invention thus resides in the concept of the bases and the acid-addition salts thereof. The novel feature of the compounds of the invention thus resides in the concept of the bases and cationic forms of the new amidinoureas and amidinothioureas and not in any particular acid moiety or acid anion associated with the salt forms of our compounds; rather, the acid moieties or anions which can be associated in the salt forms are in themselves neither novel nor critical and therefore can be any acid anion or acid-like substance capable of salt formation with bases. It will be appreciated that in aqueous solutions the base form and the acid-addition salt form of the compounds of the invention possess a common protonated cation or ammonium ion.

Thus, the acid-addition salts discussed above and claimed herein are prepared from any organic acid, inorganic acid (including organic acids having an inorganic group therein), or organo-metallic acid as exemplified by organic mono- and poly-carboxylic acids such as found, for example, in Beilstein's Organische Chemie, 4th Ed., Volumes III, IV, IX, X, XIV, XVII, XIX, XXI, XXII, and XXV; organic mono- and polysulfonic and -sulfinic acids such as found, for example in Beilstein Volumes VI, XI, XVI, and XXII; organic phosphonic and phosphinic acids such as found, for example, in Beilstein Volumes XI and XVI; organic acids of arsenic and antimony sych as found, for example, in Beilstein Volume XVI; organic heterocyclic carboxylic, sulfonic, and sulfinic acids such as found, for example in Beilstein Volumes XVIII, XXII, and XXV; acidic ion-exchange resins; and inorganic acids of any acid forming element or combination of elements such as found in Mellor, Comprehensive Treatise on Inorganic and Theoretical Chemistry, Longman's, Green and Co., New York, N.Y., Volumes I-XVI. In addition, other salt-forming compounds which are acidic in their chemical properties but which are not generally considered as acids in the same sense as carboxylic or sulfonic acids are also considered to be among the numerous acids which can be used to prepare acid-addition salts of the compounds of the invention. Thus there are also comprehended acidic phenolic compounds such as found, for example, in Volume VI or Beilstein, acidic compounds having "activated" or acidic hydrogen atoms, as for example, picrolonic acid, or barbituric acid derivatives having an acidic proton such as found, for example, in Cox et al. Medicinal Chemistry, Vol. IV, John Wiley and Sons, Inc., New York, N.Y. (1959). Also comprehended as salt forming agents are so-called Lewis acids which lack a pair of electrons in the outer "electron shell" and react with basic compounds having an unshared pair of electrons to form salts, for example boron trifluoride.

Representative acids for the formation of the acid-addition salts include formic acid, acetic acid, isobutyric acid, alpha-mercaptopropionic acid, trifluoroacetic acid, malic acid, fumaric acid, succinic acid, succinamic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicylic acid, 3,5-dinitrobenzoic acid, anthranilic acid, pamoic acid, cholic acid, 2-pyridinecarboxylic acid, 3-hydroxy-2-naphthoic acid, picric acid, quinic acid, tropic acid, 3-indoleacetic acid, barbituric acid, sulfamic acid, methanesulfonic acid, ethanesulfonic acid, isethionic acid, benzenesulfonic acid, p-toluenesulfonic acid, butylarsonic acid, methanephosphonic acid, acidic resins, hydrofluoric acid, hydrochloric acid, hydrobromic acid, hydriodic acid, perchloric acid, nitric acid, sulfuric acid, phosphoric acid, hydrocyanic acid, phosphotungstic acid, molybdic acid, arsenic acid, and the like.

The acid-addition salts are prepared in conventional fashion, for instance either by direct mixing of the acid and the base or, when this is not appropriate, by dissolving either or both of the acid and the base separately in a suitable solvent and mixing the two solutions, or by dissolving both the acid and the base together in a solvent. The resulting acid-addition salt is isolated by filtration, if it is insoluble in the reaction medium, or by evaporation of the reaction medium to leave the acid-addition salt as a residue.

Our new bases of Formulas I, II and III and the acid-addition salts thereof have biocidal and biostatic properties and are particularly useful as antibacterial and antifungal agents. Thus, when tested by standard serial dilution procedures, these compounds were found to have bactericidal, bacteriostatic, fungicidal, and fungistatic activity in vitro. Moreover, some of these compounds are effective in the control of phytopathogenic microorganisms, for instance, having useful activity against bacterial and fungal infections in plants, for example late blight (*Phytophthora infestans*) and bacterial spot (*Xantomonas vesicatoria*) on tomatoes (*Lycopersicon esculentum*) and bean rust (*Uromyces phaseoli typica*) on pinto beans (*Phaseolus vulgaris*).

The new bases of Formulas I, II and III and the acid-addition salts thereof are useful as disinfecting and sanitizing agents for application to living and non-living surfaces by conventional swabbing, padding, spraying, immersing, rinsing, and the like techniques. Depending on the particular purpose involved, the compounds are used in aqueous solution, as in water or in aqueous detergent solutions, or in the form of solutions in organic solvents.

The acid-addition salts of the bases of Formulas I, II and III are useful not only as disinfecting and sanitizing agents, as above-indicated, but are also useful as characterizing or identifying derivatives of the free bases and in isolation or purification procedures. Moreover, the acid-addition salts react with strong bases, such as alkali metal hydroxides, to generate the free bases, and accordingly all of the salts, regardless of considerations of solubility, toxicity, physical form, or the like of a particular species of acid-addition salt, are useful for the purposes of our invention since they are sources of the free bases.

It will be appreciated from the above that if one or more of the characteristics, such as solubility, molecular weight, physical appearance, toxicity, or the like of a given acid-addition salt render it unsuitable for the particular desired purpose, as for example, use as an antibacterial agent or in an isolation or purification procedure, or the like, the acid-addition salt can be converted to the free base and then to another, more suitable acid-addition salt, for instance a pharmaceutically-acceptable salt when a pharmaceutical use is involved.

The 1-(R)-amidino-3-(R')-ureas and the 1-(R)-amidino-3-(R')-thioureas of Formula I and the 1-(Y)-amidino-3-(Y')-ureas and the 1-(Y-amidino)-3-(Y')-thioureas of Formula II, except those species wherein R' and Y' are hydrogen, are obtained by interacting a 1-(R)-guanidine or a 1-(Y)-guanidine with approximately one molecular proportion of an isocyanate or isothiocyanate having the structural formula

FORMULA IV for the preparation of the Formula I compounds and having the structural formula

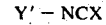

FORMULA V for the preparation of the Formula II compounds, wherein: R is hydrogen or alkyl and R' is alkyl, the total number of carbon atoms in R and R' being 8–24;

Y is a member of the group consisting of hydrogen, alkyl containing 1–18 carbon atoms, alkenyl containing 3–18 carbon atoms, alkoxyalkyl containing 3–17 carbon atoms, alkylthioalkyl containing 3–17 carbon atoms, cycloalkyl containing 3–8 carbon atoms, di(-lower alkyl)-aminoalkyl containing 4–10 carbon atoms, morpholinoalkyl containing 6–10 carbon atoms, and piperidinoalkyl containing 7–11 carbon atoms; Y' is a member of the group consisting of alkenyl containing 3–18 carbon atoms, alkoxyalkyl containing 3–17 carbon atoms, alkylthioalkyl containing 3–17 carbon atoms, cycloalkyl containing 3–8 carbon atoms, di(-lower alkyl)aminoalkyl containing 4–10 carbon atoms, morpholinoalkyl containing 6–10 carbon atoms, and piperidinoalkyl containing 7–11 carbon atoms; and X in each instance is a member of the group consisting of oxygen and sulfur. In a convenient method of carrying out this reaction, sodium and dry acetone are mixed together, and then the guanidine in the form of its hydrochloride or sulfate is added, and this is followed by the isocyanate or isothiocyanate reactant; approximately equimolar amounts each of the sodium, the 1-(R or Y)-guanidine salt, and the isocyanate or isothiocyanate are used, and the method can be carried out at room temperature.

The 1-(R)-amidino-3-(R')-ureas of Formula I wherein R' is hydrogen and the 1-(Y)-3-(Y')-ureas of Formula II wherein Y' is hydrogen are obtained by hydrolyzing with a strong acid a 1-(R)-3-cyanoguanidine having the structural formula

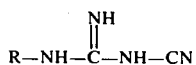

FORMULA VI or a 1-(Y)-3-cyanoguanidine having the structural formula

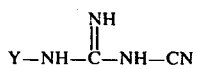

FORMULA VII wherein R is alkyl containing 8–24 carbon atoms and Y is a member of the group consisting of alkenyl containing 3–18 carbon atoms, alkoxyalkyl containing 3–17 carbon atoms, alkylthioalkyl containing 3–17 carbon atoms, cycloalkyl containing 3–8 carbon atoms, di(-lower alkyl)aminoalkyl containing 4–10 carbon atoms, morpholinoalkyl containing 6–10 carbon atoms, and piperidinoalkyl containing 7–11 carbon atoms. Conveniently, this hydrolysis is carried out by refluxing the 1-(R or Y)-3-cyanoguanidine with concentrated hydrochloric acid.

The 1-(R)-amidino-3-(R')-thioureas of Formula I wherein R' is hydrogen and the 1-(Y)-amidino-3-(Y')-thioureas of Formula II wherein Y' is hydrogen are obtained by interacting one equivalent of a 1-(R)-3-cyanoguanidine having the structural formula V or a 1-(Y)-3-cyanoguanidine having the structural Formula VI, as hereinabove defined, with two equivalents of hydrogen sulfide. Conveniently the cyanoguanidine is heated with a saturated lower alkanolic solution of hydrogen sulfide at 70°–80°C. in a closed vessel. For best results, the reaction mixture is heated for 48 hours or longer.

The 1-(Y'')-amidino-3-(Y''')-ureas and the 1-(Y''-amidino)-3-(Y''')-thioureas of Formula III are obtained by interacting a 1-(Y'')-guanidine with approximately one molecular proportion of an isocyanate or isothiocyanate having the structural formula $$Y''' - NCX$$

FORMULA VIII wherein Y'', Y''', and X have the same respective meanings indicated hereinabove in relation to Formula III. In a convenient method of carrying out this reaction, sodium and dry acetone are mixed together, and then the guanidine in the form of its hydrochloride or sulfate is added, and this is followed by the isocyanate or isothiocyanate reactant; approximately equimolar amounts each of the sodium, the 1-(Y'')-guanidine salt, and the isocyanate or isothiocyanate are used, and the method can be carried out at room temperature.

The intermediates required for the preparation of our new compounds are all old and well-known classes of compounds and are readily obtained by conventional preparative procedures. Thus, for example, the isocyanates and isothiocyanates of Formulas IV, V and VIII are obtained by interaction of phosgene or thiophosgene with a primary amine having the formula R'-NH$_2$, Y'-NH$_2$ or Y'''-NH$_2$, or the hydrochlorides thereof, wherein R', Y', and Y''' have the same significance as indicated hereinabove in connection with Formulas IV, V and VIII. The 1-(R)-3-cyanoguanidines of Formula VI and the 1-(Y)-3-cyanoguanidines of Formula VII are obtained, for example, by interaction of dicyanamide, or metal salt thereof, with a primary amine having the formula R-NH$_2$ or Y-NH$_2$ or acid-addition salt thereof, wherein R and Y have the same significance indicated hereinabove in connection with Formulas VI and VII, respectively. The 1-(R, Y and Y'')-guanidines include guanidine itself, which is readily available, and the substituted guanidines which are obtained, for example, by interaction of ammonium chloride with a substituted cyanamide having the formula R-NH-CN, Y-NH-CN or Y''-NH-CN, or by interaction of 2-methyl-2-thiopseudourea sulfate with a primary amine having the formula R-NH$_2$, Y-NH$_2$ or Y''-NH$_2$, wherein R, Y and Y''have the same significance indicated hereinabove in connection with Formula VI, VII and VIII, respectively.

We especially prefer those compounds of this invention in which R and R' in Formula I contain a total of 9-16 carbon atoms, Y and Y' in Formula II, and Y'' and Y''' in Formula III contain a total of 9–16 carbon atoms since these preferred compounds have particularly high antibacterial and antifungal activities and hence have been found to be particularly useful as antibacterial and antifungal agents.

The chemical structures of the compounds of this invention followed from the modes of preparation from the elementary analyses of the products, and from spectral data on the compounds.

Our invention is illustrated by the following examples without, however, being limited thereto.

EXAMPLE 1

A. 4.1 g. of sodium was added to 200 ml. of dry acetone and the mixture was refluxed for ten minutes and after the resulting mixture cooled to room temperature there was added in one portion, with strong stirring, 19.1 g. of guanidine hydrochloride. The resulting reaction mixture was stirred for forty-five minutes, and there was added dropwise, at room temperature and over a period of one-half hour, a solution of 23.2 g. of n-octyl isocyanate in 100 ml. of dry acetone. The reaction mixture thus obtained was stirred at room temperature for three hours and then was evaporated under reduced pressure to reduce its volume by half and poured into 250 ml. of cold water. (In following this procedure in the preparation of related species of this invention, it was found in some instances that instead of pouring the reaction product into water it was desirable and in some cases necessary for ready recovery of the product to evaporate the reaction mixture to dryness and then purify the resulting residue). The mixture was chilled in a refrigerator overnight. The solid precipitate which formed was collected on a filter, washed with cold water, and dried. The dry solid was dissolved in 250 ml. of warm diethyl ether, and the solution was treated with decolorizing charcoal and filtered. The filtrate was warmed to evaporate off about 100 ml. of ether and cold petroleum ether was added gradually until a slight turbidity was produced. The mixture was cooled and the solid which precipitated was collected on a filter and dried in a vacuum desiccator. The solid thus obtained, which weighed 28.5 g., was recrystallized from diethyl ether-petroleum mixture to yield 24.1 g. of 1-amidino-3-n-octylurea, having the structural formula

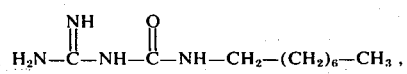

as a white crystalline solid which melted at 102°–106°C. The solubility of this base in water at 25°C. was less than 0.25 per cent. It was soluble in 95 per cent ethyl alcohol at 25°C. to the extent of 5 per cent (w/v); a precipitate formed when the 5 per cent alcoholic solution was diluted with four volumes of water.

B. When an equivalent amount of n-octyl isothiocyanate is substituted for the n-octyl isocyanate in the procedure described in part A above, there is obtained as the product 1-amidino-3-n-octylthiourea, having the structural formula

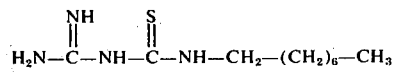

C. When an equivalent amount of iso-octyl isocyanate is substituted for the n-octyl isocyanate in the procedure described in part A above, there is obtained as the product 1-amidino-3-iso-octylurea, having the structural formula

D. When an equivalent amount of tert-octyl isothiocyanate is substituted for the n-octyl isocyanate in the procedure described in part A above, there is obtained as the product 1-amidino-3-tert-octylthiourea, having the structural formula

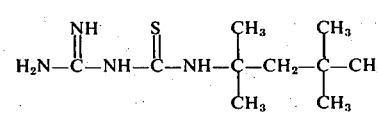

E. When an equivalent amount of cyclohexyl isocyanate is substituted for the n-octyl isocyanate in the procedure described in part A above, there is obtained as the product 1-amidino-3-cyclohexylurea, having the structural formula

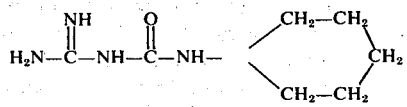

F. When an equivalent amount of 2-diethylaminoethyl isocyanate is substituted for the n-octyl isocyanate in the procedure described in part A above, there is obtained as the product 1-amidino-3-(2-diethylaminoethyl)urea, having the structural formula

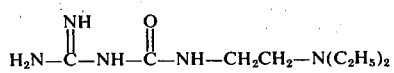

G. When an equivalent amount of 5-morpholinoamyl isocyanate is substituted for the n-octyl isocyanate in the procedure described in part A above, there is obtained as the product 1-amidino-3-(5-morpholinoamyl)urea, having the structural formula

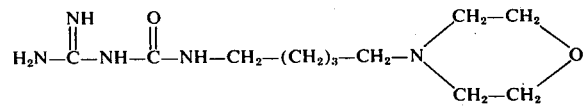

H. When an equivalent amount of 3-piperidinopropyl isocyanate is substituted for the n-octyl isocyanate in the procedure described in part A above, there is obtained as the product 1-amidino-3-(3-piperidinopropyl)urea, having the structural formula

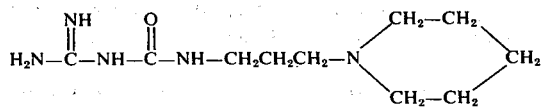

EXAMPLE 2

A. Proceeding in a manner similar to that described above in Example 1, and using 3.2 g. of sodium, 14.3 g. of guanidine hydrochloride, and 18.3 g. of n-nonyl isocyanate, there was obtained 18.5 g. of 1-amidino-3-n-nonylurea, having the structural formula

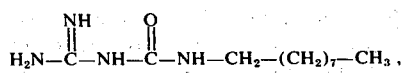

as a white crystalline solid which melted at 104°–105°C.

The solubility of this base in water at 25°C. was less than 0.25 per cent. In 95 per cent ethyl alcohol at 25°C., it was soluble to the extent of 5 per cent (w/v); a precipitate formed when the 5 per cent alcoholic solution was diluted with four volumes of water.

B. By treatment of 1-amidino-3-n-nonylurea with hydrobromic acid in isopropyl alcohol there was obtained 1-amidino-3-n-nonylurea hydrobromide as a white crystalline solid which melted at 80°–82°C. This salt was soluble in water at 25°C. to the extent of 1 per cent. The pH of the 1 per cent solution was 4.7; when the pH was gradually raised by addition of N/10 sodium hydroxide solution, a precipitate formed at pH 6.5.

C. When an equivalent amount of iso-nonyl isothiocyanate is substituted for the n-nonyl isocyanate in the procedure described in part A above, there is obtained as the product 1-amidino-3-iso-nonylthiourea, having the structural formula

EXAMPLE 3

A. Proceeding in a manner similar to that described above in Example 1, and using 3.2 g. of sodium, 14.3 g. of guanidine hydrochloride, and 18.3 g. of n-decyl isocyanate, there was obtained 17.5 g. of 1-amidino-3-n-decylurea, having the structural formula

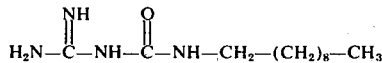

as a white crystalline solid which melted at 110°–112°C. The solubility of this base in water at 25°C. was less than 0.25 per cent. In 95 per cent ethyl alcohol at 25°C., it was soluble to the extent of 5 per cent (w/v); a precipitate formed when the 5 per cent alcoholic solution was diluted with four volumes of water.

B. The hydrobromide of the above base was prepared as follows: 10 g. of 1-amidino-3-n-decylurea was dissolved in 80 ml. of warm methyl alcohol. The resulting solution was cooled to room temperature, and a solution of hydrogen bromide in diethyl ether was added until the pH of the mixture was approximately 6. The ether was evaporated off under reduced pressure, and to the oily residue was added 200 ml. of anhydrous diethyl ether. The mixture was filtered to collect the solid which formed. The solid thus collected, which weighed 12 g., was dissolved in 30 ml. of warm methyl alcohol, 400 ml. of anhydrous diethyl ether was added, and the mixture was cooled. The solid which precipitated from solution was collected on a filter, dried overnight in a vacuum oven at 35°C. There was thus obtained 9.4 g. of 1-amidino-3-n-decylurea hydrobromide as a white crystalline solid which melted at 78°–82°C. The solubility of this hydrobromide in water at 25°C. was 0.5 per cent. The pH of the 0.5 per cent aqueous solution was 5.0; when N/10 sodium hydroxide solution was gradually added to this solution, a precipitate formed at pH 5.5.

C. To a solution of 17 g. of 1-amidino-3-n-decylurea in 150 ml. of methyl alcohol there was added 5 per cent sulfuric acid until the pH of the mixture was approximately 3. The mixture was cooled, and the solid which precipitated was collected on a filter and recrystallized from 90 ml. of methyl alcohol to yield 18 g. of 1-amidino-3-n-decylurea sulfate [$(H_2N\text{-}C(=NH)\text{-}NH\text{-}CO\text{-}NH\text{-}C_{10}H_{21})_2 \cdot H_2SO_4$] which melted at 131°–132°C. The solubility of this sulfate in water at 25°C. was less than 0.25 per cent; and its solubility in 95 per cent ethyl alcohol at 25°C. was less than 1 per cent (w/v).

EXAMPLE 4

Proceeding in a manner similar to that described above in part A of Example 1, and using 3.6 g. of sodium, 16.2 g. of guanidine hydrochloride, and 29.8 g. of n-decyl isothiocyanate, there was obtained 16.0 g. of 1-amidino-3-n-decylthiourea, having the structural formula

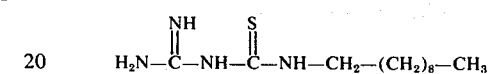

as a white crystalline solid which melted at 71°–72°C. The solubility of this base in water at 25°C. was less than 0.25 per cent. In 95 per cent ethyl alcohol, at 25°C. it was soluble to the extent of 5 per cent (w/v); a precipitate formed when the 5 per cent alcoholic solution was diluted with four volumes of water.

EXAMPLE 5

A. Proceeding in a manner similar to that described above in Example 1, and using 4.3 g. of sodium, 19.1 g. of guanidine hydrochloride, and 29.6 g. of n-undecyl isocyanate, there was obtained 30 g. of 1-amidino-3-n-undecylurea, having the structural formula

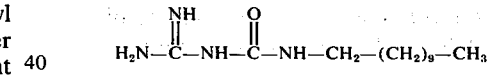

as a white crystalline solid which melted at 109°–110°C. The solubility of this base in water at 25°C. was less than 0.25 per cent. In 95 per cent ethyl alcohol at 25°C., it was soluble to the extent of 5 per cent (w/v); a precipitate formed when the 5 per cent alcoholic solution was diluted with four volumes of water.

B. By adding to a solution of 10 g. of 1-amidino-3-n-undecylurea in 70 ml. of methyl alcohol sufficient ethereal solution of hydrogen bromide to give a mixture having pH 5, and isolating and recrystallizing the resultant product from methyl alcohol-diethyl ether mixture, there was obtained 10.5 g. of 1-amidino-3-N-undecylurea hydrobromide as a white crystalline solid which melted at 82°–83°C. The solubility of this hydrobromide in water at 25°C. was less than 0.25 per cent. It was soluble in 95 per cent ethyl alcohol at 25°C. to the extent of 5 per cent (w/v); a precipitate formed when the 5 per cent alcoholic solution was diluted with four volumes of water.

EXAMPLE 6

A. Proceeding in a manner similar to that described above in Example 1, and using 2.7 g. of sodium, 12.4 g. of guanidine hydrochloride, and 21.1 g. of n-dodecyl isocyanate, there was obtained 23.0 g. of 1-amidino-3-n-dodecylurea, having the structural formula

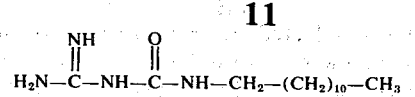

as a white crystalline solid which melted at 100°–103°C. The solubility of this base in water at 25°C. was less than 0.25 per cent. Its solubility in 95 per cent ethyl alcohol at 25°C. was less than 1 per cent (w/v).

Interaction of this base with hydrogen bromide yielded 1-amidino-3-n-dodecylurea hydrobromide as a white crystalline solid which melted at 87°–89°C. The solubility of this hydrobromide in water at 25°C. was less than 0.25 per cent. It was soluble in 95 per cent ethyl alcohol at 25°C. to the extent of 1 per cent (w/v); no precipitate formed when the 1 per cent alcoholic solution was diluted with four volumes of water, the pH of the thus-diluted solution being 4.1.

EXAMPLE 7

Proceeding in a manner similar to that described above in Example 1, and using 2.7 g. of sodium, 12.4 g. of guanidine hydrochloride, and 22.7 g. of n-dodecyl isothiocyanate, there was obtained 12.8 g. of 1-amidino-3-n-dodecylthiourea, having the structural formula

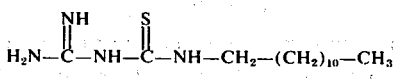

as a white crystalline solid which melted at 75°–80°C. The solubility of this base in water at 25°C. was less than 0.25 per cent. In 95 per cent ethyl alcohol, at 25°C., it was soluble to the extent of 1 per cent (w/v); a precipitate formed when the 1 per cent alcoholic solution was diluted with four volumes of water.

EXAMPLE 8

A. Proceeding in a manner similar to that described above in Example 1, and using 2.7 g. of sodium, 12.4 g. of guanidine hydrochloride, and 23.9 g. of n-tetradecyl isocyanate, there was obtained 20 g. of 1-amidino-3-n-tetradecylurea, having the structural formula

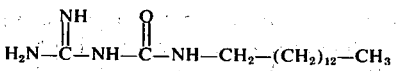

as a white crystalline solid which melted at 100°–104°C. The solubility of this base in water at 25°C. was less than 0.25 per cent; and its solubility in 95 per cent ethyl alcohol at 25°C. was less than 1 per cent (w/v).

B. Proceeding in a manner similar to that described in Example 1, and using 2.7 g. of sodium, 12.4 g. of guanidine hydrochloride, and 25.6 g. of n-tetradecyl isothiocyanate, there was obtained 13.7 g. of 1-amidino-3-N-tetradecylthiourea, having the structural formula

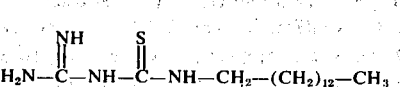

as a white crystalline solid which melted at 77°–79°C. The solubility of this base in water was less than 0.25 per cent. In 95 per cent ethyl alcohol at 25°C., it was soluble to the extent of 5 per cent (w/v); a precipitate formed when the 5 per cent alcoholic solution was diluted with four volumes of water.

EXAMPLE 9

A. Proceeding in a manner similar to that described above in Example 1, and using 3.4 g. of sodium, 15.3 g. of guanidine hydrochloride, and 30.1 g. of n-hexadecyl isocyanate, there was obtained 23.7 g. of 1-amidino-3-n-hexadecylurea, having the structural formula

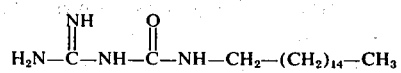

as a white crystalline solid which melted at 107°–109°C. The solubility of this base in water at 25°C. was less than 0.25 per cent. Its solubility in 95 per cent ethyl alcohol at 25°C. was less than 1 per cent (w/v).

B. When an equivalent amount of n-hexadecyl isothiocyanate is substituted for the n-hexadecyl isocyanate in the procedure described in part A above, there is obtained as the product 1-amidino-3-N-hexadecylthiourea, having the structural formula

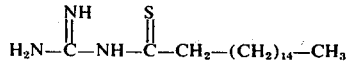

EXAMPLE 10

A. Proceeding in a manner similar to that described above in Example 1, and using 3.2 g. of sodium, 14.3 g. of guanidine hydrochloride, and 18.1 g. of 9-decenyl isocyanate, there was obtained 16 g. of 1-amidino-3-(9-decenyl)urea, having the structural formula

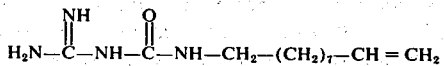

as a white crystalline solid which melted at 94°-97°C. The solubility of this base in water at 25°C. was less than 0.25 per cent. In 95 per cent ethyl alcohol at 25°C., it was soluble to the extent of 5 per cent (w/v); a precipitate formed when the 5 per cent alcoholic solution was diluted with four volumes of water.

B. When an equivalent amount of 9-decenyl isothiocyanate is substituted for the 9-decenyl isocyanate in the procedure described in part A above, there is obtained as the product 1-amidino-3-(9-decenyl)thiourea, having the structural formula

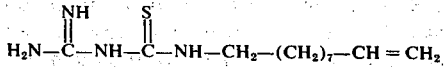

C. When an equivalent amount of 9-octadecenyl isocyanate is substituted for the 9-decenyl isocyanate in the procedure described in part A above, there is obtained as the product 1-amidino-3-(9-octadecenyl)urea, having the structural formula

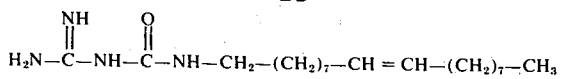

D. When an equivalent amount of 9-octadecenyl isothiocyanate is substituted for the 9-decenyl isocyanate in the procedure described in part A above, there is obtained as the product 1-amidino-3-(9-octadecenyl)thiourea, having the structural formula

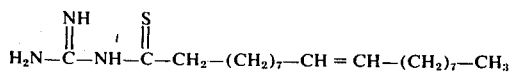

EXAMPLE 11

A. Proceeding in a manner similar to that described above in Example 1, and using 2.72 g. of sodium, 11.2 g. of guanidine hydrochloride, and 18.0 g. of 3-(n-octyloxy)propyl isocyanate, there was obtained 4.0 g. of 1-amidino-3-[3-(n-octyloxy)propyl]urea, having the structural formula

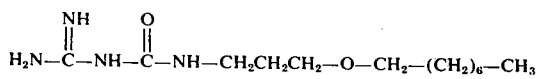

as an off-white powder which melted at 74°–76°C. This base was soluble in a dilute acidic solution (prepared by mixing 0.36 ml. of N/2 hydrochloric acid and 0.14 ml. of water) at 25°C. to the extent of 10 per cent. The pH of a 1 per cent solution in the dilute acid was 2.2; no precipitate formed when the pH of this solution was adjusted to 7.0 by addition of N/10 sodium hydroxide solution.

B. When an equivalent amount of 3-(n-octyloxy)propyl isothiocyanate is substituted for the 3-(n-octyloxy)propyl isocyanate in the procedure described in part A above, there is obtained as the product 1-amidino-3-[3-(n-octyloxy)propyl]-thiourea, having the structural formula

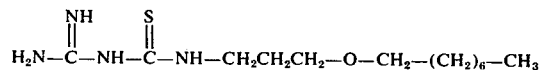

C. When an equivalent amount of 6-methoxyhexyl isocyanate is substituted for the 3-(n-octyloxy)propyl isocyanate in the procedure described in part A above, there is obtained as the product 1-amidino-3-(6-methoxyhexyl)urea, having the structural formula

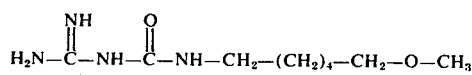

D. When an equivalent amount of 8-(n-propyloxy)octyl isosthiocyanate is substituted for the 3-(n-octyloxy)propyl isocyanate in the procedure described in part A above, there is obtained as the product 1-amidino-3-[8-(n-propyloxy)octyl]-thiourea, having the structural formula

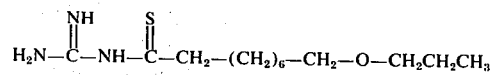

EXAMPLE 12

A. Proceeding in a manner similar to that described above in Example 1, and using 2.4 g. of sodium, 11.2 g. of guanidine hydrochloride, and 18.0 g. of 3-(n-decyloxy)propyl isocyanate, there was obtained 11 g. of 1-amidino-3-[3-(n-decyloxy)propyl]urea, having the structural formula

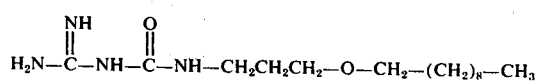

as a cream colored powder which melted at 78°–82°C. The solubility of this base in water at 25°C. was less than 0.25 per cent. In 95 per cent ethyl alcohol at 25°C., it was soluble to the extent of 5 per cent (w/v); a precipitate formed when the 5 per cent alcoholic solution was diluted with four volumes of water.

B. When an equivalent amount of 3-(n-decyloxy)propyl isothiocyanate is substituted for the 3-(n-decyloxy)propyl isocyanate in the procedure described in part A above, there is obtained as the product 1-amidino-3-[3-(n-decyloxy)-propyl]thiourea, having the structural formula

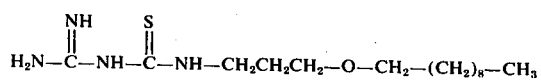

C. When an equivalent amount of 7-(n-decyloxy)-heptyl isocyanate is substituted for the 3-(n-decyloxy)-propyl isocyanate in the procedure described in part A above, there is obtained as the product 1-amidino-3-[7-(n-decyloxy)heptyl]-urea, having the structural formula

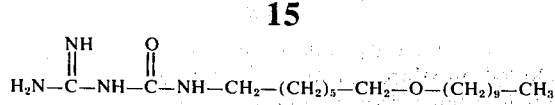

EXAMPLE 13

A. Proceeding in a manner similar to that described above in Example 1, and using 2.5 g. of sodium, 11.1 g. of guanidine hydrochloride, and 20 g. of 3-(n-decylthio)propyl isocyanate, there was obtained 18.8 g. of 1-amidino-3-[3-(n-decylthio)propyl]urea, having the structural formula

as a white solid which melted at 89°–92°C. The solubility of this base in water at 25°C. was less than 0.25 per cent. In 95 per cent ethyl alcohol at 25°C., it was soluble to the extent of 5 per cent (w/v); a precipitate formed when the 5 per cent alcoholic solution was diluted with four volumes of water.

B. When an equivalent amount of 3-(n-decylthio)propyl isothiocyanate is substituted for the 3-(n-decylthio)propyl isocyanate in the procedure described in part A above, there is obtained as the product 1-amidino-3-[3-(n-decylthio)-propyl]thiourea, having the structural formula

C. When an equivalent amount of 4-(n-propylthio)butyl isocyanate is substitiuted for the 3-(n-decylthio)propyl isocyanate in the procedure described in part A above, there is obtained as the product 1-amidino-3-[4-n-propylthio)butyl]-urea, having the structural formula

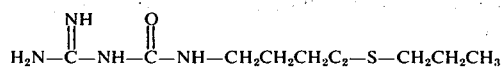

EXAMPLE 14

A. A mixture of 22.4 g. of 1-n-decyl-3-cyanoquanidine, 78 ml. of isopropyl alcohol, and 16 ml. of concentrated hydrochloric acid was refluxed for 30 minutes, after which another 6 ml. of concentrated hydrochloric acid was added, and the mixture was refluxed for 2 hours. The reaction mixture was cooled and was then evaporated under reduced pressure until the mixture began to foam. There was then added 400 ml. of warm water, and the resulting solution was filtered warm through diatomaceous earth repeatedly until a clear filtrate was obtained. The filtrate, which contained 1-(n-decylamidino)urea hydrochloride dissolved therein, was cooled, and the pH was adjusted to approximately 6 by addition of N sodium hydroxide solution, thereby to neutralize the hydrochloride and generate the free base, 1-(n-decylamidino)urea, having the structural formula

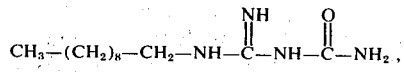

and then a solution of 20 g. of sodium nitrate in 40 ml. of water was added with vigorous stirring. The mixture was chilled for several hours, and the solid which precipitated was collected on a filter and washed with dilute nitric acid and water. The solid was dried under reduced pressure at room temperature (about 25°C.) for 4 hours and at 30°C. for 3 hours. This product, which weighed 36 g., was recrystallizied from 400 ml. of acetonitrile and then from 70 ml. of isopropyl alcohol to yield 12.0 g. of 1-(n-decylamidino)urea nitrate, as a white crystalline solid which melted at 125°–127°C. The solubility of this nitrate in water was less than 0.25 per cent, and in 95 per cent ethyl alcohol its solubility was less than 1 per cent (w/v).

B. When an equivalent amount of 1-n-octyl-3-cyanoguanidine is substituited for the 1-n-decyl-3-cyanoguanidine in the procedure described in part A above, thre are obtained as the products 1-(n-octylamidino)urea, having the structural formula

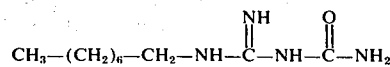

and the nitrate salt thereof.

C. When an equivalent amount of 1-(9-decenyl)-3-cyanoguanidine is substituted for the 1-n-decyl-3-cyanoguanidine in the procedure described in part A above, there are obtained as the products 1-(9-decenylamidino)urea, having the structural formula

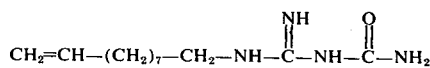

and the nitrate salt thereof.

D. When an equivalent amount of 1-[3-(iso-decyloxy)-propyl]-3-cyanoguanidine is substituted for the 1-n-decyl-3-cyanoguanidine in the procedure described in part A above, there are obtained as the products 1-[3-iso-decyloxy)propylamidino]urea, having the structural formula

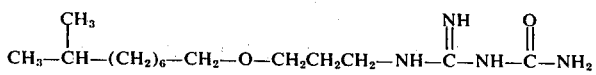

and the nitrate salt thereof.

E. When an equivalent amount of 1-[4-(tert-octylthio)-butyl]-3-cyanoguanidine is substituted for the 1-n-decyl-3-cyanoguanidine in the procedure described in part A above, there are obtained as the products 1-[4-(tert-octylthio)butylamidino]urea, having the structural formula

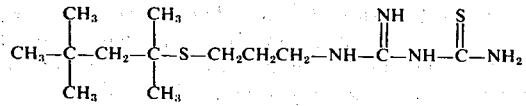

and the nitrate salt thereof.

F. When an equivalent amount of 1-cyclooctyl-3-cyanoguanidine is substituted for the 1-n-decyl-3-cyanoguanidine in the procedure described in part A above, there are obtained as the products 1-(cyclooctylamidino)urea, having the structural formula

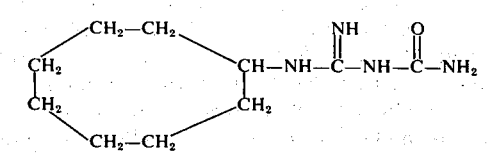

and the nitrate salt thereof.

G. When an equivalent amount of 1-(2-morpholinoethyl)-3-cyanoguanidine is substitiuted for the 1-n-decyl-3-cyanoguanidine in the procedure described in part A above, there are obtained as the products 1-[(2-morpholinoethyl)amidino]urea, having the structural formula

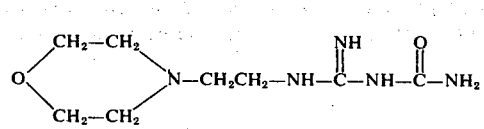

and the nitrate salt thereof.

H. When an equivalent amount of 1-(6-piperidinohexyl)-3-cyanoguanidine is substituted for the 1-n-decyl-3-cyanoguanidine in the procedure described in part A above, there are obtained as the products 1-[(6-piperidinohexyl)amidino]urea, having the structural formula

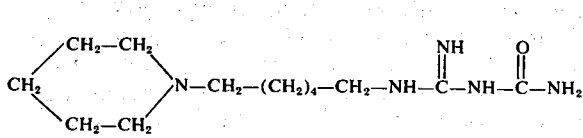

and the nitrate salt thereof.

EXAMPLE 15

Proceeding in a manner similar to that described above in Example 14, and using 25.2 g. of 1-n-dodecyl-3-cyanoguanidine, 68 ml. of isopropyl alcohol, and 16 ml. of concentrated hydrochloric acid, there were obtained 1-(n-dodecylamidino)urea hydrochloride, the free base 1-(n-dodecylamidino)urea having the structural formula

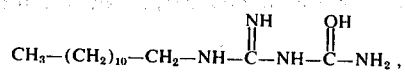

and 1-(n-dodecylamidino)urea nitrate. The nitrate was a white crystalline solid which melted at 109°-110°C. The solubility of the nitrate in water at 25°C. was less than 0.25 per cent, and in 95 per cent ethyl alcohol its solubilitiy was less than 1 per cent.

EXAMPLE 16

Proceeding in a manner similar to that described above in Example 14, and using 20 g. of 1-n-tetradecyl-3-cyanoguanidine, 70 ml. of isopropyl alcohol, and 9 ml. of hydrochloric acid, there was obtained 1-(n-tetradecylamidino)-urea hydrochloride, the free base 1-(n-tetradecylamidino)urea having the structural formula

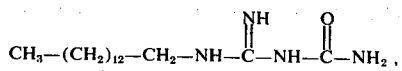

and 1-(n-tetradecylamidino)urea nitrate. The nitrate (11 g. yield) was dissolved in methyl alchol and sodium hydroxide solution was added to regenerate the free base, 1-n-tetradecyl-3-cyanoguanidine, which was dissolved in methyl alcohol and treated with ethereal hydrogen bromide solution to yield 5.2 g. of 1-n-tetradecyl-3-cyanoguanidine hydrobromide as a white crystalline solid which melted at 116°-118°C. The solubility of the hydrobromide in water at 25°C. was less than 0.25 per cent. In 95 per cent ethyl alcohol at 25°C., the hydrobromide was soluble to the extent of 5 per cent (w/v); a precipitate formed slowly when the 5 per cent alcoholic solution was diluted with four volumes of water.

EXAMPLE 17

A. A mixture of 70 g. of 1-n-octyl-3-cyanoguanidine and 800 ml. of a saturated (at 0°C.) solution of hydrogen sulfide in methyl alcohol is heated at 70°-80°C. in a closed vessel for forty-eight hours. The reaction mixture thus obtained is evaporated to dryness under reduced pressure leaving a residue consisting of crude 1-(n-octylamidino)thiourea, having the structural formula

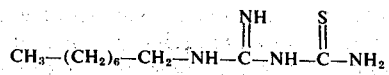

Recrystallization of this product yields the pure base.

B. When an equivalent amount of 1-n-heptadecyl-3-cyanoguanidine is substituted for the 1-n-octyl-3-cyanoguanidine in the procedure described in part A above, there is obtained as the product 1-(n-heptadecylamidino)thiourea having the structural formula

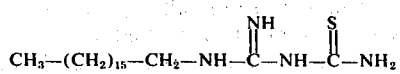

C. When an equivalent amount of 1-[6-(n-hexyloxy)-hexyl]-3-cyanoguanidine is substitiued for the 1-n-octyl-3-cyanoguanidine in the procedure described in part A above, there is obtained as the product 1-[6-(n-hexyloxy)hexylamidino]-thiourea, having the structural formula

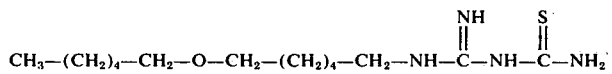

D. When an equivalent amount of 1-[6-(n-nonylthio)hexyl]-3-cyanoguanidine is substituted for the 1-n-octyl-3-cyanoguanidine in the procedure described in part A above, there is obtained as the product 1-[6-(n-nonylthio)hexylamidino]thiourea, having the structural formula

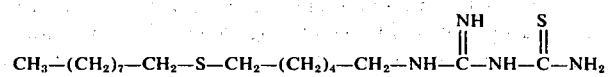

E. When an equivalent amount of 1-(7-tetradecenyl)-3-cyanoguanidine is substituted for the 1-n-octyl-3-cyanoguanidine in the procedure described in part A above, there is obtained as the product 1-(7-tetradecenyl)amidinothiourea, having the structural formula

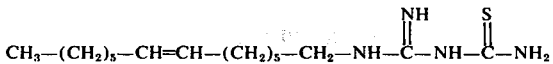

EXAMPLE 18

A. To a solution obtained by dissolving 4.6 g. of sodium in 300 ml. of dry acetone there was added 32.8 g. of n-butylguanidine sulfate and the resulting mixture was stirred for one hour at room temperature. There was then added dropwise, over a period of one hour, a solution of 19.8 g. of n-butyl isocyanate in 200 ml. of dry acetone, and the mixture thus obtained was stirred overnight at room temperature. (In some instances it was found preferable to use an equivalent amount of tert-butyl alcohol instead of acetone both in the reaction with sodium and as the reaction solvent.) The reaction mixture was evaporated under reduced pressure to reduce its volume by half, after which it was poured into 250 ml. of cold water. (In the preparation of related species of this invention by this procedure, it was found in some instances that instead of pouring the reaction product into water it was desirable and in some cases necessary for ready recovery of the product to evaporate the reaction mixture to dryness and then purify the resulting residue). The red oil which separated from solution was washed twice with water and was then dissolved in diethyl ether. The ethereal solution was dried over anhydrous calciuim sulfate, and the ether was then evaporated from the solution to yield 1-n-butylamidino-3-n-butylurea, having the structural formula

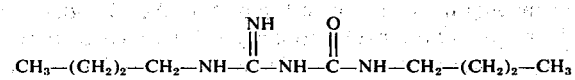

as an oil. This base was dissolved in anhydrous diethyl ether and was converted to its sulfate by addition of a 5 per cent ethereal sulfuric acid solution. The resulting solution was evaporated under reduced pressure, and the pasty residue thus obtained was dissolved in 200 ml. of methyl alcohol. The methanolic solution was treated with decolorizing charcoal and after removal of the charcoal the solution was evaporated under reduced pressure. The residue was dissolved in 200 ml. of isopropyl alcohol and the solution was evaporated under reduced pressure. The sticky residue was dissolved in 200 ml. of methyl alcohol and the methanolic solution was saturated with gaseous ammonia. The mixture was filtered to remove ammonium sulfate and the filtrate was evaporated under reduced pressure to yield a red oil. This oil was dissolved in 100 ml. of anhydrous diethyl ether, 75 ml. of petroleum ether was added, and the resulting solid precipitate was collected on a filter and dried under redued pressure for four hours at 40°C. This product, which weighed 21.7 g., was recrystallized from benzene (100 ml.)-petroleum ether (80 ml.) and then from 700 ml. of anhydrous diethyl ether. There was thus obtained 10.3 g. of 1-n--butylamidino-3-n-butylurea as a white crystalline solid which melted at 82°–94°C. From the ethereal mother liquor there was recovered 3.1 g. of the same product. The solubility of this base in water was less than 0.5 per cent. It was soluble in 95 per cent ethyl alcohol to the extent of 5 per cent (w/v); on addition of four volumes of water to the 5 per cent alcoholic solution, the diluted solution, which had a pH of 8.9, remainde clear.

B. When an equivalent amount of n-butyl isothiocyanate is used in place of the n-butyl isocyanate in the procedure described in part A above, the product obtained is 1-n-butylamidino-3-n-butylthiourea, having the structural formula

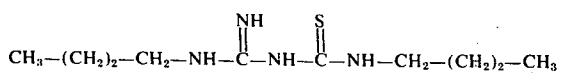

C. When an equivalent amount of 9-decenyl isocyanate is used in place of the n-butyl isocyanate in the procedure described in part A above, the product obtained is 1-n-butylamidino-3-(9-decenyl)urea, having the structural formula

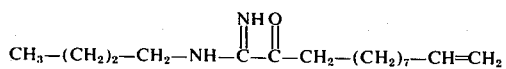

D. Using the procedure described above in part A, when an equivalent amount of 4-morpholinobutylguanidine sulfate is substituted for the n-butylguanidine and an equivalent amount of cyclohexyl isocyanate is substituted for the n-butyl isocyanate, the product obtained is 1-(4-morpholinobutylamidino)-3-cyclohexylurea, having the structural formula

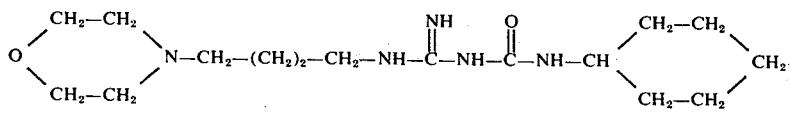

E. Using the procedure described in part A, when an equivalent amount of 12-ethoxydodecylguanidine sulfate is substituted for the n-butylguanidine and an equivalent amount of 4-(n-octylthio)butyl isocyanate is substituted for the n-butyl isocyanate, the product obtained is 1-(12-ethoxydodecylamidino)-3-[4(n-octylthio)butyl]urea, having the structural formula

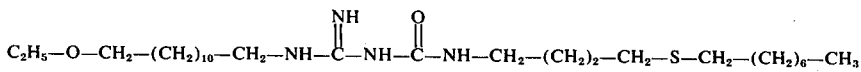

EXAMPLE 19

Proceeding in a manner similar to that described above in part A of Example 18, and using 4.5 g. of sodium, 35.6 g. of n-amylguanidine sulfate, and 22.6 g. of n-amyl isocyanate, there was obtained 14.2 g. of 1-n-amylamidino-3-n-amylurea having the structural formula

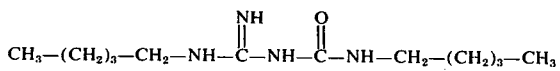

as a white crystalline solid which melted at 89°–91°C. The solubility of this base in water at 25°C. was less than 0.25 per cent. In 95 per cent ethyl alcohol at 25°C. it was soluble to the extent of 5 per cent (w/v); a precipitate formed when the 5 per cent alcoholic solution was diluted with four volumes of water.

EXAMPLE 20 proceeding in a manner similar to that described above in part A of Example 18, and using 4.5 g. of sodium, 38.4 g. of n-hexylguanidine sulfate, and 19.8 g. of n-butyl isocyanate, there was obtained 21 g. of 1-n-hexylamidino-3-n-butylurea having the strucutural formula

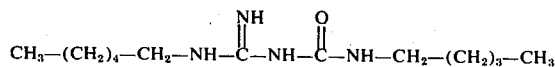

as an off-white crystalline powder which melted at 96–99°C. The solubility of this base in water at 25°C. was less than 0.25 per cent. In 95 per cent ethyl alcohol at 25°C. it was soluble to the extent of 5 per cent (w/v); a precipitate formed when the 5 per cent alcoholic solution was diluted with four volumes of water.

EXAMPLE 21

Proceeding in a manner similar to that described above in part A of Example 18, and using 3.44 g. of sodium, 28.8 g. of n-hexylguanidine sulfate, and 17.0 g. of n-amyl isocyanate, there was obtained 20.0 g. of 1-n-hexylamidino-3-n-amylurea having the structural formula

CH$_3$—(CH$_2$)$_4$—CH$_2$—NH—C(=NH)—NH—C(=O)—NH—CH$_2$—(CH$_2$)$_3$—CH$_3$ as a white crystalline solid which melted at 74°–75°C.

The solubility of this base in water at 25°C. was less than 0.25 per cent. In 95 per cent ethyl alcohol at 25°C. it was soluble to the extent of 5 per cent (w/v); a precipitate formed when the 5 per cent alcoholic solution was diluted with four volumes of water.

EXAMPLE 22

A. Proceeding in a manner similar to that described above in part A of Example 18, and using 4.5 g. of sodium, 38.4 g. of n-hexylguanidine sulfate, and 25.4 g. of n-hexyl isocyanate, there was obtained 11.1 g. of 1-n-hexylamidino-3-n-hexylurea having the structural formula

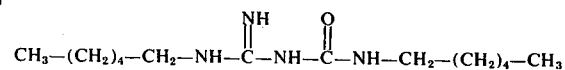

as a white crystalline solid which melted at 75–78°C. The solubility of this base in water at 25°C. was less than 0.25 per cent. In 95 per cent ethyl alcohol at 25°C. it was soluble to the extent of 5 per cent (w/v); a precipitate formed when the 5 per cent alcoholic solution was diluted with four volumes of water.

B. By treatment of 6 g. of 1-n-hexylamidino-3-n-hexylurea with hydrogen chloride in methanolic solution there was obtained 6.3 g. of 1-n-hexylamidino-3-n-hexylurea hydrochloride as a white crystalline solid which melted at 60°–62°C. The solubility of this hydrochloride in water at 25°C. was less than 0.25 per cent. It was soluble in 95 per cent ethyl alcohol at 25°C. to the extent of 5 per cent (w/v); a precipitate formed slowly when the 5 per cent alcoholic solution was diluted with four volumes of water, the pH of the thus-diluted solution being 4.4.

C. By treatment of 6 g. of 1-n-hexylamidino-3-n-hexylurea in methanolic solution with an ethereal solution of hydrogen bromide there was obtained 6.5 g. of 1-n-hexylamidino-3-n-hexylurea hydrobromide as a white crystalline solid which melted at 56°–60°C. The solubility of this hydrobromide in water at 25°C. was less than 0.25 per cent. It was soluble in 95 per cent ethyl alcohol at 25°C. to the extent of 5 per cent (w/v); a precipitate formed slowly when the 5 per cent alcoholic solution was diluted with four volumes of water, the pH of the thus-diluted solution being 4.3.

D. By treatment of 6 g. of 1-n-hexylamidino-3-n-hexylurea with 85 per cent phosphoric acid in methanolic solution there was obtained 6.2 g. of 1-n-hexylamidino-3-n-hexylurea phosphate as a white crystalline solid which melted at 106°–109°C. The solubility of this phosphate in water at 25°C. was less than 0.25 per cent. It was soluble in 95 per cent ethyl alcohol at 25°C. to the extent of 5 percent (w/v); a precipitate formed when the 5 per cent alcoholic solution was diluted with four volumes of water.

E. By treatment of 6 g. of 1-n-hexylamidino-3-n-hexylurea with 70 per cent glycolic acid in methanolic solution there was obtained 5.5 g. of 1-n-hexylamidino-3-n-hexylurea glycolate as a white crystalline solid which melted at 94°–98°C. The solubility of this glycolate in water at 25°C. was less than 0.25 per cent. It was soluble in 95 per cent ethyl alcohol at 25°C. to the extent of 5 per cent (w/v); a precipitate formed when the 5 per cent alcoholic solution was diluted with four volumes of water.

F. By treatment of 6 g. of 1-n-hexylamidino-3-n-hexylurea with 85 per cent lactic acid in methanolic solution there was obtained 5 g. of 1-n-hexylamidino-3-n-hexylurea lactate as a white crystalline solid which melted at 65°–69°C. The solubility of this lactate in a dilute acidic solution (prepared by mixing 0.28 ml. of N/2 hydrochloric acid solution with 19.72 ml. of water) at 25°C. was less than 0.25 per cent. It was soluble in 95 per cent ethyl alcohol at 25°C. to the extent of 5 per cent (w/v); a precipitate formed when the 5 per cent alcoholic solution was diluted with four volumes of water.

EXAMPLE 23

Proceeding in a manner similar to that described above in part A of Example 18, and using 3.44 g. of sodium, 30.9 g. of n-heptylguanidine sulfate, and 19.1 g. of n-hexyl isocyanate, there was obtained 26.2 g. of 1-n-heptylamidino-3-n-hexylurea having the structural formula

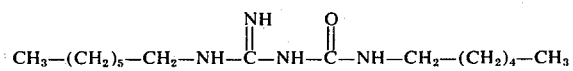

as a white crystalline solid which melted at 68°–72°C. The solubility of this base in a dilute acidic solution (prepared by mixing 0.36 ml. of N/2 hydrochloric acid and 9.64 ml. of water) at 25°C. was less than 0.25 per cent. In 95 per cent ethyl alcohol at 25°C. it was soluble to the extent of 5 per cent (w/v); a precipitate formed when the 5 per cent alcoholic solution was diluted with four volumes of water.

EXAMPLE 24

Proceeding in a manner similar to that described above in part A of Example 18, 2.7 g. of sodium was dissolved in 250 ml. of dry acetone, 25 g. of n-heptylguanidine sulfate was added to the solution, the mixture was stirred for 15 hours at room temperature; and then a solution of 16.9 g. of n-heptyl isocyanate in 200 ml. of acetone was added dropwise, and the reaction mixture was stirred for 3 hours at room temperature. The reaction mixture was evaporated to half-volume under reduced pressure and the mixture was stored in a refrigerator for 2 weeks. The solid which had precipitated was collected on a filter, was washed with water and a few ml. of acetonitrile, and dried overnight in a desiccator. The yellowish product thus obtained, which weighed 32.2 g., was mixed with 30 ml. of cold acetonitrile, and the solid was collected on a filter, dried overnight in a desiccator, and then recrystallized from acetonitrile to yield 23 g. of 1-n-heptylamidino-3-n-heptylurea having the structural formula

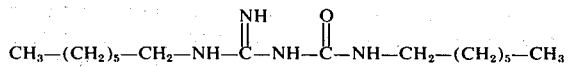

as a white crystalline solid which melted at 56°–59°C. This base in methanolic solution was treated with ethereal hydrogen chloride solution to yield 21.3 g. of 1-n-heptylamidino-3-n-heptylurea hydrochloride as a white crystalline solid which melted at 71°–75°C. The solubility of this hydrochloride in dilute aqueous alkali (prepared by mixing 0.30 ml. of N/2 sodium hydroxide solution with 19.70 ml. of water) at 25°C. was less than 0.25 per cent. In 95 per cent ethyl alcohol at 25°C. this salt was soluble to the extent of 5 per cent (w/v); a precipitate formed when the 5 per cent alcoholic solution was diluted with four volumes of water.

EXAMPLE 25

A. 3.68 g. of sodium and 1050 ml. of dry t-butyl alcohol were heated together under reflux with vigorous stirring for about 2 hours. The liquid was cooled to approximately 28°C. and then 25 g. of (3-morpholinopropyl)-guanidine sulfate was added in one portion. After stirring the mixture for thirty minutes, a solution of 9.85 g. of n-octyl isocyanate in 100 ml. of t-butyl alcohol was added dropwise over a period of twenty minutes. The resulting reaction mixture was stirred for two and one-half hours and allowed to stand overnight. The mixture was concentrated on a water bath at 35°–45°C. The residue was mixed with 250 ml. of acetonitrile and allowed to stand overnight. The mixture was filtered to remove 16.2 g. of solid, and the acetonitrile was distilled from the filtrate to yield 23 g. of a lightbrown syrup consisting of crude 1-[(3-morpholinopropyl)-amidino]-3-n-octylurea, having the structural formula tained 1-[(3-morpholinopropyl)amidino]-3-n-decylurea having the structural formula

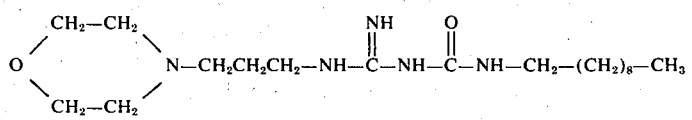

and the dihydrochloride thereof. The dihydrochloride

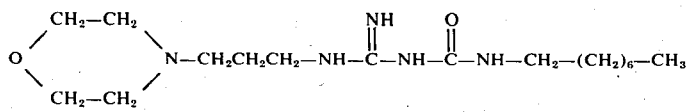

Approximately 18 g. of this syrup was mixed with 500 ml. of anhydrous diethyl ether, the mixture was filtered through diatomaceous earth, the filtrate was acidified by addition of 22 ml of 4.3N alcoholic hydrogen chloride solution, and the mixture was chilled overnight. The solid which had precipitated was then collected on a filter. This solid, which weighed 17.7 g., was recrystallized from isopropyl alcohol, with charcoaling, to yield 12.8 g. of solid which was then recrystallized again from isopropyl alcohol. There was thus obtained 9.5 g. of 1-[(3-morpholinopropyl)amidino]-3-n-octylurea dihydrochloride as a white powder which melted at 141°–143°C. (dec.). This salt was soluble in water at 25°C. to the extent of 20 per cent. The pH of the 1 per cent aqueous solution was 4.0; when the pH of this solution was gradually raised by addition of N/10 sodium hydroxide solution, no precipitate formed at pH 7.

B. When an equivalent amount of (2-piperidinoethyl)-guanidine sulfate is used instead of (3-morpholinopropyl)-guanidine sulfate in the procedure described in part A above, the products obtained are 1-[(2-piperidinoethyl)amidino]-3-n-octylurea, having the structural formula was obtained as a white powder which weighed 15.2 g. and which melted at 134°–135°C. This salt was soluble in water at 25°C. to the extent of 20 per cent; the pH of the 1 per cent aqueous solution was 4.6, and when the pH was gradually raised by addition of N/10 sodium hydroxide solution no precipitate formed at pH 7.

EXAMPLE 27

Proceeding in a manner similar to that described above in Example 18A, and using 2.3 g. of sodium, 22 g. of n-octylguanidine sulfate, and 15.5 g. of n-octyl isocyanate, there was obtained 26 g. of 1-n-octylamidino-3-n-octylurea having the structural formula

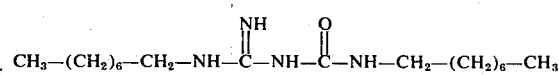

as a white crystalline solid which melted at 60°–62°C. The solubility of this base in water at 25°C. was less than 0.25 per cent. IN 95 per cent ethyl alcohol it was soluble to the extent of 5 per cent; a precipitate formed when the 5 per cent ethanolic solution was diluted with

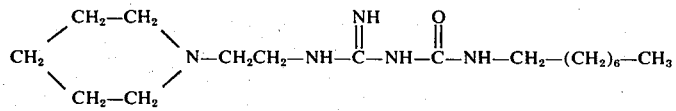

and the dihydrochloride thereof.

C. Following the procedure described in part A above but using an equivalent amount of 4-piperidinobutyl isocyanate in place of n-octyl isocyanate, there are obtained as the products 1-[(3-morpholinopropyl)amidino]-3-(4-piperidinobutyl)-urea, having the structural formula four volumes of water.

EXAMPLE 28

A. Proceeding in a manner similar to that described above in Example 1, and using 3.4 g. of sodium, 14.3 of guanidine hydrochloride, and 27.7 g. of n-nonyl isothiocyanate, there was obtained 1-amidino-3-n-nonyl-

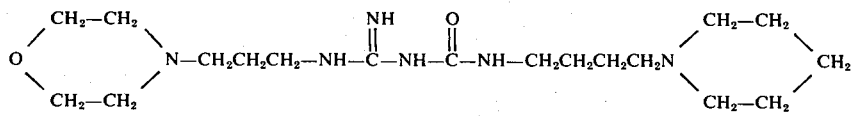

and the trihydrochloride thereof.

EXAMPLE 26

Proceeding in a manner similar to that described above in part A of Example 25, and using 3.68 g. of sodium, 25 g. of (3-morpholinopropyl)guanidine sulfate, and 11.6 g. of n-decyl isocyanate, there were obtained thiourea, having the structural formula

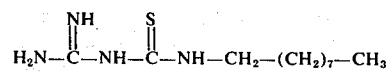

as a red oil.

B. By treatment of 1-amidino-3-n-nonylthiourea with ethereal hydrogen chloride there was obtained 1-amidino-3-n-nonylthiourea hydrochloride as a white crystalline solid which melted at 79°–81°C. The solubility of this salt in water at 25°C. was less than 0.25 per cent; and its solubility in 95 per cent ethyl alcohol at 25°C. was less than 1 per cent (w/v).

EXAMPLE 29

Proceeding in a manner similar to that described above in Example 1, and using 2.5 g. of sodium, 10.4 of guanidine hydrochloride, and 24.5 g. of n-undecyl isothiocyanate, there was obtained 15.9 g. of 1-amidino-3-n-undecylthiourea, having the structural formula

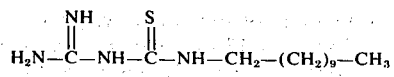

as a white crystalline solid which melted at 71°–72°C. The solubility of this base in a dilute acidic solution (0.40 ml. of N/2 hydrochloric acid plus 19.60 ml. of water) was less than 0.25 per cent. In 95 per cent ethyl alcohol at 25°C., it was soluble to the extent of less than 1 per cent (w/v).

EXAMPLE 30

Proceeding in a manner similar to that described above in Example 1, and using 2.9 g. of sodium, 12.9 g. of guanidine hydrochloride, and 17.9 g. of 3-(n-heptyloxy)-propyl isocyanate, there was obtained 1-amidino-3-[3-(n-heptyloxy)propyl)urea, having the structural formula

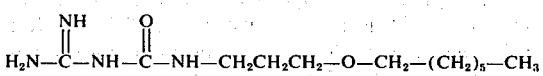

as a white powder which melted at 72-74°C. This base was soluble in a dilute acidic solution (0.39 ml. of N/2 hydrochloric acid plus 0.61 ml. of water) at 25°C. to the extent of 5 per cent. In 95 per cent ethyl alcohol at 25°C., it was soluble to the extent of 5 per cent (w/v); a precipitate formed when the 5 per cent alcoholic solution was diluted with four volumes of water.

EXAMPLE 31

Proceeding in a manner similar to that described above in Example 1, and using 2.6 g. of sodium, 11.2 g. of guanidine hydrochloride, and 18.0 g. of 3-(n-nonyloxy)-propyl isocyanate, there was obtained 1-amidino-3-[3-(n-nonyloxy)propyl]urea having the structural formula

as a white crystalline solid which melted at 77°–78°C. This base was soluble in a dilute acidic solution (0.35 ml. of N/2 hydrochloric acid plus 19.65 ml. of water) to less than 0.25 per cent. In 95 per cent ethyl alcohol at 25°C, it was soluble to the extent of 5 per cent (w/v); a precipitate formed when the 5 per cent alcoholic solution was diluted with four volumes of water.

EXAMPLE 32

A. Proceeding in a manner similar to that described above in Example 1, and using 2.8 g. of sodium, 12.0 g. of guanidine hydrochloride, and 32.0 g. of 3-(n-undecyloxy)-propyl isocyanate, there was obtained 15.7 g. of 1-amidino-3-[3-(n-undecyloxy)propyl]urea, having the structural formula

as a white powder which melted at 72°–78°C.

B. Interaction of this base with hydrogen chloride yielded 1-amidino-3-[3-(n-undecyloxy)propyl]urea hydrochloride as a white powder which melted at 66°–69°C. This hydrochloride was soluble in water at 25°C. to the extent of 20 per cent. The pH of a 1 per cent aqueous solution was 3.7; when N/10 sodium hydroxide solution was gradually added to this solution, a precipitate formed at pH 5.5.

EXAMPLE 33

A. Proceeding in a manner similar to that described above in Example 1, and using 3.0 g. of sodium, 13.0 g. of guanidine hydrochloride, and 36.6 g. of 3-(n-dodecyloxy)-propyl isocyanate, there was obtained 1-amidino-3-[3-(n-dodecyloxy)propyl]urea, having the structural formula

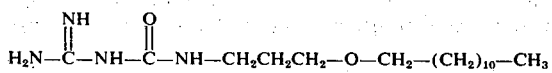

as a white powder which melted at 76°–80°C.

B. By treatment of 6.5 g. of 1-amidino-3-[3-(n-dodecyloxy)propyl]urea in ethyl alcohol solution of hydrogen chloride, there was obtained 5.0 g. of 1-amidino-3-[3-(n-dodecyloxy)propyl]urea hydrochloride as a white powder which melted at 59°–61°C. This hydrochloride was soluble in water at 25°C. to the extent of 20 per cent. The pH of a 1 per cent aqueous solution was 3.9; when N/10 sodium hydroxide solution was gradually added to this solution, a precipitate formed at pH 4.8.

EXAMPLE 34

Proceeding in a manner similar to that described above in Example 1, and using 2.3 g. of sodium, 9.5 g. of guanidine hydrochloride, and 20.0 g. of 3-(n-hexylthio)propyl isocyanate, there was obtained 1-amidino-3-[3-(n-hexylthio)-propyl]urea, having the structural formula

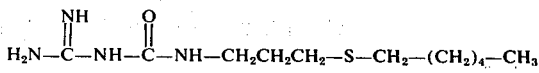

as a white crystalline solid which melted at 71°–73°C. The solubility of this base in a dilute acidic solution (0.78 ml. of N/2 hydrochloric acid plus 19.72 ml. of water) at 25°C. was less than 0.25 per cent. In 95 per cent ethyl alcohol at 25°C., it was soluble to the extent of 5 per cent (w/v); a precipitate formed when the 5 per cent alcoholic solution was diluted with four volumes of water.

EXAMPLE 35

Proceeding in a manner similar to that described above in Example 1, and using 1.06 g. of sodium, 4.45 g. of guanidine hydrochloride, and 10.0 g. of 3-(n-heptylthio)propyl isocyanate, there was obtained 1-amidino-3-[3-(n-heptylthio)propyl]urea having the structural formula

as a white crystalline solid which melted at 79°–82°C. The solubility of this base in a dilute acidic solution (0.40 ml. of N/2 hydrochloric acid plus 19.60 ml. of water) at 25°C. was less than 0.25 per cent. In 95 per cent ethyl alcohol at 25°C., it was soluble to the extent of 5 per cent (w/v); a precipitate formed when the 5 per cent alcoholic solution was diluted with four volumes of water.

EXAMPLE 36

Proceeding in a manner similar to that described above in Example 1, and using 3.4 g. of sodium, 14.3. g. of guanidine hydrochloride, and 34.3. g. of 3-(n-octylthio)propyl isocyanate, there was obtained 22.0 g. of 1-amidino-3-[3-(n-octylthio)propyl]urea having the structural formula

as a white crystalline solid which melted at 84°–85°C. The solubility of this base in a dilute acidic solution (0.35 ml. of N/2 hydrochloric acid plus 19.65 ml. of water) at 25°C. was less than 0.25 per cent. In 95 per cent ethyl alcohol at 25°C., it was soluble to the extent of 5 per cent (w/v); a precipitate formed when the 5 per cent alcoholic solution was diluted with four volumes of water.

EXAMPLE 37

Proceeding in a manner similar to that described in Example 1, and using 2.3 g. of sodium, 9.5 g. of guanidine hydrochloride, and 22.9 g. of 3-(n-nonylthio)-propyl isocyanate, there was obtained 19.7 g. of 1-amidino-3-[3-(n-nonylthio)propyl]urea, having the structural formula

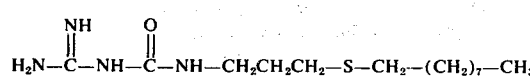

as a white crystalline solid which melted at 86°–88°C. The solubility of this base in a dilute acidic solution (0.34 ml. of N/2 hydrochloric acid plus 19.66 ml. of water) at 25°C. was less than 0.25 per cent. In 95 per cent ethyl alcohol at 25°C., it was soluble to the extent of 5 per cent (w/v); a precipitate formed when the 5 per cent alcoholic solution was diluted with four volumes of water.

EXAMPLE 38

Proceeding in a manner similar to that described above in Example 1, and using 2.3 g. of sodium, 9.5 g. of guanidine hydrochloride, and 27.1 g. of 3-(n-undecylthio)propyl isocyanate, there was obtained 16.6 g. of 1-amidino-3-[3-(n-undecylthio)propyl]urea, having the structural formula

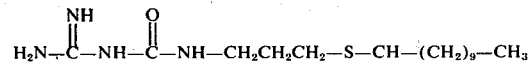

as a white crystalline solid which melted at 91–93°C. The solubility of this base in a dilute acidic solution (0.30 ml. of N/2 hydrochloric acid plus 19.70 ml. of water) at 25°C. was less than 0.25 per cent. In 95 per cent ethyl alcohol at 25°C., it was soluble to the extent of 5 per cent (w/v); a precipitate formed when the 5 per cent alcoholic solution was diluted in four volumes of water.

EXAMPLE 39

Proceeding in a manner similar to that described above in Example 1, and using 2.3 g. of sodium, 9.5 g. of guanidine hydrochloride, and 28.5 g. of 3-(n-dodecylthio)propyl isocyanate, there was obtained 28.5 g. of 1-amidino-3-[3-(n-dodecylthio)propyl]urea, having the structural formula

as a white crystalline solid which melted at 91°–92°C. The solubility of this base in a dilute acidic solution (0.30 ml. of N/2 hydrochloric acid plus 19.70 ml. of water) at 25°C. was less than 0.25 per cent. In 95 per cent ethyl alcohol at 25°C., it was soluble to the extent of 5 per cent (w/v); a precipitate formed when the 5 per cent alcoholic solution was diluted with four volumes of water.

EXAMPLE 40

Proceeding in a manner similar to that described above in part A of Example 25, and using 1.96 g. of sodium, 12.5 g. of (3-morpholinopropyl)guanidine sulfate, and 7.2 g. of n-nonyl isocyanate, there was obtained 1-[(3-morpholinopropyl)amidino]-3-n-nonylurea having the structural formula

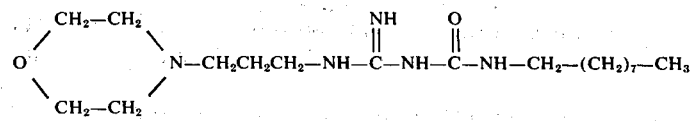

and the dihydrochloride thereof. The dihydrochloride was obtained as a white powder which melted at 139°–141°C. This salt was soluble in water at 25°C. to the extent of 20 per cent; the pH of the 1 per cent aqueous solution was 3.5, and when the pH was gradually raised by addition of N/10 sodium hydroxide solution, no precipitate formed at pH 7.

EXAMPLE 41

Proceeding in a manner similar to that described above in part A of Example 25, and using 1.96 g. of sodium, 12.5 g. of (3-morpholinopropyl)guanidine sulfate, and 8.4 g. n-undecylisocyanate, there was obtained 1-[(3-morpholinopropyl)amidino]-3-n-undecylurea having the structural formula

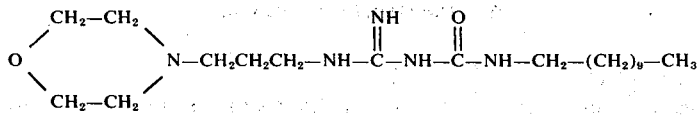

and the dihydrochloride thereof. The dihydrochloride was obtained as a white powder which weighed 9.7 g. and which melted at 143°–145°C. The salt was soluble in water at 25°C. to the extent of 20 per cent; the pH of the 1 per cent aqueous solution was 3.8, and when the pH was gradually raised by addition of N/10 sodium hydroxide solution, no precipitate formed at pH 6.3.

EXAMPLE 42

Proceeding in a manner similar to that described above in part A of Example 25, and using 1.96 g. of sodium, 12.5 g. of (3-morpholinopropyl)guanidine sulfate, and 8.95 g. of n-dodecylisocyanate, there was obtained 1-[(3-morpholinopropyl)amdino]-3-n-dodecylurea having the structural formula

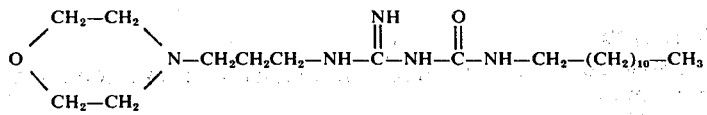

and the dihydrochloride thereof. The dihydrochloride was obtained as a white powder which weighed 5.9 g. and which melted at 132°–135°C. This salt was soluble in water at 25°C. to the extent of 20 per cent; the pH of the 1 per cent aqueous solution was 3.8, and when the pH was gradually raised by addition of N/10 sodium hydroxide solution, no precipitate formed at pH 7.6.

Proceeding in accordance with the procedures described hereinabove and using the appropriate reactants, there are obtained the following further illustrative species of the compounds of Formulas I, II and III of the instant invention:

1. 1-n-hexylamidino-3-(3,3-dimethylallyl)urea
2. 2 1-(4-dimethylaminobutylamidino)-3-cyclopropylurea
3. 1-(9-decenylamidino)-3-(9-decenyl)urea
4. 1-cyclohexylamidino-3-cyclopentylurea
5. 1-cycloheptylamidino-3-[4-(n-amyloxy)butyl]urea
6. 1-(3-morpholinopropylamidino)-3-(3-octenyl)thiourea
7. 1-(3-piperidinopropylamidino)-3-(3-piperidinopropyl)thiourea
8. 1-n-hexylamidino-3-n-hexylthiourea
9. 1-n-heptylamidino-3-n-heptylthiourea
10. 1-tert-octylamidino-3-(3-morpholinopropyl)urea
11. 1-[3-(n-octyloxy)propylamidino]-3-(3-morpholinopropyl)urea
12. 1-(cyclobutylamidino)-3-[3-(n-decyloxy)propyl]thiourea
13. 1-(8-dimethylaminooctylamidino)-3-[3-(n-decylthio)propyl]thiourea
14. 1-n-octylamidino-3-(3-propoxypropyl)urea
15. 1-iso-heptylamidino-3-[4-(propylthio)butyl]urea
16. 1-n-heptylamidino-3-(2-diisopropylaminoethyl)thiourea
17. 1-cyclopentylamidino-3-n-undecylurea
18. 1-cyclopropylamidino-3-(3-piperidinobutyl)urea
19. 1-(3-morpholinopropylamidino)-3-(4-morpholinobutyl)urea
20. 1-(2-diethylaminoethylamidino)-3-(2-diethylaminoethyl)-thiourea
21. 1-(2-dimethylaminopropylamidino)-3-(3-morpholinopropyl)-thiourea
22. 1-[3-(n-decylthio)propylamidino]-3-[3-(n-decylthio)-propyl]urea
23. 1-[3-(n-decylthio)propylamidino]-3-cyclohexylurea
24. 1-[4-(n-nonylthio)butylamidino]-3-(5-morpholinoamyl)urea
25. 1-[3-(n-octyloxy)propylamidino]-3-[3-(n-octyloxy)propyl]-urea
26. 1-[3-(n-heptyloxy)propylamidino]-3-(10-undecenyl)urea
27. 1-cyclopentylamidino-3-(3,3-dimethylallyl)urea
28. 1-[(3-hexenyl)amidino]-3-[3-(n-dodecylthio)-propyl]urea
29. 1-(3-di-n-butylaminopropylamidino)-3-(4-octenyl)urea
30. 1-methallylamidino-3-(3-piperidinopropyl)urea
31. 1-(2-piperidinoethylamidino)-3-(3-diethylaminopropyl)-thiourea
32. 1-(3-piperidinopropylamidino)-3-[4-(n-propyloxy)butyl]urea
33. 1-methylamidino-3-(2-ethylhexyl)urea
34. 1-ethylamidino-3-isohexylthiourea
35. 1-n-heptylamidino-3-methylurea
36. 1-(n-tetracosanylamidino)urea
37. 1-amidino-3-n-tetracosanylurea
38. 1-n-docosanylamidino-3-methylthiourea
39. 1-[(2-ethylhexyl)amidino]urea
40. 1-amidino-2-(2-ethylhexyl)urea Following are representative results obtained when the compounds prepared in accordance with the instant invention were tested in vitro by standard serial dilution procedures for bacteriostatic (Bs), bactericidal (Bc), fungistatic (Fs), and fungicidal (Fc) properties; these results are expressed as minimum concentration of the test compound, in parts per million, required for no growth of the test organism. For example, in antibacterial tests, using *Staphylococcus aureus* 209, *Salmonella typhosa* Hopkins, *Clostridium welchii* M, and *Pseudomonas aeruginosa* 211, the results obtained were as follows:

| Compound of Example No. | Staph. aureus | | Sal. typosa | | Cl. welchii | | Ps. aerug. | |
|---|---|---|---|---|---|---|---|---|
| | Bs | Bc | Bs | Bc | Bs | Bc | Bs | Bc |
| 1A | 25 | 25 | 10 | 25 | 10 | 25 | 25 | 25 |
| 2A | 5 | 7.5 | 5 | 5 | 7.5 | 7.5 | 7.5 | 7.5 |
| 3A | 2.5 | 10 | 2.5 | 10 | 2.5 | 2.5 | 5 | 10 |
| 4 | 5 | 10 | 25 | 25 | 2.5 | 2.5 | 75 | >100 |
| 5A | 2.5 | 2.5 | 5 | 5 | 2.5 | 2.5 | 250 | 1000 |
| 6A | 2.5 | 75 | 5 | 75 | 50 | 50 | 100 | >100 |
| 7 | 25 | 25 | 25 | 75 | 2.5 | 2.5 | 250 | 250 |
| 8A | 5 | 100 | 50 | >100 | 7.5 | 7.5 | 750 | >1000 |
| 8B | 10 | 50 | 750 | >1000 | 5 | 5 | 500 | >1000 |
| 9A | 500 | >1000 | 1000 | >1000 | 25 | 25 | 1000 | >1000 |
| 10A | 7.5 | 7.5 | 7.5 | 7.5 | 7.5 | 7.5 | 7.5 | 25 |
| 11A | 50 | 50 | 10 | 25 | 10 | 25 | 50 | 50 |
| 12A | 5 | 7.5 | 5 | 7.5 | 5 | 5 | 25 | 25 |
| 13A | 7.5 | 25 | 7.5 | 10 | 5 | 5 | 50 | 75 |
| 14A (·HNO$_3$) | 10 | 50 | 10 | 25 | 10 | 10 | 50 | 50 |
| 15 (·HNO$_3$) | 7.5 | 75 | 7.5 | 10 | 5 | 5 | 50 | 75 |
| 15 (·HBr) | 7.5 | 25 | 10 | 50 | 5 | 5 | 75 | 100 |
| 18A | 250 | 250 | 250 | 500 | 25 | 250 | 500 | 500 |
| 19 | 25 | 50 | 25 | 50 | 7.5 | 25 | 250 | 250 |
| 20 | 50 | 50 | 25 | 50 | 5 | 25 | 250 | 250 |
| 21 | 25 | 25 | 25 | 25 | 2.5 | 2.5 | 100 | >100 |
| 22A | 5 | 5 | 7.5 | 10 | 2.5 | 5 | 50 | 75 |
| 22B | 10 | 20 | 5 | 7.5 | 150 | * 200 | 100 | 100 |
| 22C | 10 | 100 | 7.5 | 15 | 150 | * 200 | 100 | 100 |
| 22D | 15 | 15 | 7.5 | 10 | 100 | * 200 | 100 | 150 |
| 22E | 10 | 15 | 7.5 | 10 | 100 | * 200 | 100 | 150 |
| 22F | 10 | 20 | 7.5 | 15 | 150 | * 200 | 100 | 100 |
| 23 | 5 | 5 | 5 | 5 | 2.5 | 2.5 | 50 | 100 |
| 24 | 5 | 25 | 5 | 7.5 | 2.5 | 2.5 | 50 | 75 |
| 25 (·2HCl) | 50 | 75 | 50 | 50 | 10 | 10 | >100 | — |
| 26 (·2HCl) | 7.5 | 25 | 10 | 25 | 2.5 | 2.5 | 100 | 100 |
| 27 | 7.5 | 50 | 7.5 | 10 | 5 | 5 | >100 | — |
| 28B (·HCl) | 5 | — | 10 | ** — | 50 | * — | 75 | — |
| 29 | 0.75 | — | 25 | ** — | 75 | * — | >100 | — |
| 30 | 25 | 50 | 50 | ** 50 | 75 | * >100 | 50 | 100 |
| 31 | 5 | 10 | 5 | ** 10 | 100 | * >100 | 25 | 50 |
| 32B (·HCl) | — | — | 50 | ** — | >100 | * — | 75 | — |
| 33B (·HCl) | 5 | — | 25 | ** — | >100 | * — | 75 | — |
| 34 | 25 | — | 10 | — | 75 | * — | 50 | — |
| 35 | 5 | 25 | 7.5 | ** 7.5 | 50 | * 75 | 50 | 50 |
| 36 | 5 | 7.5 | 7.5 | ** 7.5 | 75 | * 100 | 25 | 50 |
| 37 | 5 | 10 | 25 | ** 25 | 100 | * >100 | 25 | 50 |
| 38 | 7.5 | 50 | 50 | ** 50 | >100 | * — | 75 | 100 |
| 39 | 10 | 75 | 50 | ** 75 | >100 | * — | 75 | >100 |
| 40 (·2HCl) | 12.5 | — | 12.5 | ** — | >100 | * — | 100 | — |
| 41 (·2HCl) | 2.5 | — | 25 | ** — | >100 | * — | >100 | — |
| 42 (·2HCl) | 5 | — | 2.5 | ** — | >100 | * — | >100 | — |

\* *Proteus vulgaris* ATCC 9920 was used instead of *Cl. welchii*.
\** *Escherichia coli* was used instead of *Sal. typhosa*.

In antifungal tests, using Trichophyton mentagrophytes, Aspergillus niger, and Monilia albicans, the following results were obtained:

| Compound of Example No. | T. mentag. | | As. niger | | Mon. alb. | |
|---|---|---|---|---|---|---|
| | Fs | Fc | Fs | Fc | Fs | Fc |
| 1A | 100 | 100 | — | — | — | — |
| 3A | 10 | 10 | 1000 | >1000 | 100 | 1000 |
| 5A | 10 | 10 | 1000 | 1000 | 100 | 1000 |
| 7 | 10 | 100 | 100 | 100 | 100 | 100 |
| 8B | 100 | 100 | 1000 | >1000 | 1000 | >1000 |
| 11A | 100 | 100 | 100 | 100 | 100 | 100 |
| 12A | 100 | 100 | 100 | 100 | 100 | 100 |
| 13A | 100 | 100 | 100 | 100 | 100 | 100 |
| 14A (.NHO$_3$) | 100 | 100 | >100 | — | 100 | >100 |
| 15 (.HNO$_3$) | 10 | 10 | 100 | >100 | 10 | 100 |
| 16 (.HBr) | 10 | 100 | 100 | 100 | 10 | 100 |
| 18A | 1000 | 1000 | 1000 | 1000 | 1000 | 1000 |
| 21 | 100 | 100 | 100 | 100 | 100 | 100 |
| 22A | 100 | 100 | 100 | >100 | 100 | 100 |
| 23 | 100 | 100 | 100 | 100 | 100 | 100 |
| 24 | 10 | 10 | 100 | 100 | 10 | 100 |
| 25 | 100 | 100 | 1000 | 1000 | 1000 | 1000 |
| 26 | 100 | 100 | 100 | 100 | 100 | 100 |
| 27 | 100 | 100 | 100 | >100 | >100 | — |
| 28B (.HCl) | 5 | — | 12.5 | — | 12.5 | — |
| 29 | 5 | — | 100 | — | 50 | — |
| 30 | 75 | — | >100 | — | 100 | — |
| 31 | 25 | — | 50 | — | 25 | — |
| 32B (.HCl) | 75 | — | >100 | — | 100 | — |
| 33B (.HCl) | 50 | — | >100 | — | 50 | — |
| 34 | 50 | — | 100 | — | 100 | — |
| 35 | 25 | 25 | 75 | 75 | 50 | 50 |
| 40 (.2HCl) | 50 | — | >100 | — | >100 | — |
| 41 (.2HCl) | 7.5 | — | 50 | — | 75 | — |

| Compound of Example No. | T. mentag. Fs | As. niger Fe | Fs | Mon. alb. Fc | Fs | Fc |
|---|---|---|---|---|---|---|
| 42 (.2HCl) | 12.5 | — | >100 | — | 50 | — |

When an aqueous solution of one pound of 1-amidino-3-n-decylurea hydrobromide in 100 gallons of water was sprayed onto the foliage of tomato plants, 68 per cent protection was afforded against infection by *Xanthomonas vesicatoria* (bacterial spot). When the same compound at one-quarter pound per 100 gallons of water was similarly applied to tomato plants, 99 per cent of the plants were protected against infection by *Phytophthora infestans* (late blight). And when this same compound at one-quarter pound per 100 gallons of water was similarly applied to pinto beans, 86 per cent protection was afforded against infection by *Uromyces phaseoli typica* (bean rust).

1-Amidino-3-n-dodecylthiourea was found to afford good protection against bacterial spot in tomato plants.

In commercial paper pulp having a native population of approximately one million organisms per gram, all organisms in the pulp were killed within one hour by 10 parts per million of 1-amidino-3-n-undecylurea hydrobromide, thus indicating the usefulness of this compound as a slime control agent in paper making.

We claim:
1. 1-Amidino-3-decylurea.
2. 1-Amidino-3-undecylurea.
3. 1-Amidino-3-dodecylurea.

* * * * *